United States Patent [19]

Dürr

[11] Patent Number: 4,649,212
[45] Date of Patent: Mar. 10, 1987

[54] NOVEL PHENOXYPHENYLAMINO ACID DERIVATIVES, THE PRODUCTION THEREOF, COMPOSITIONS CONTAINING THEM AND USE THEREOF

[75] Inventor: Dieter Dürr, Bottmingen, Switzerland

[73] Assignee: Ciba-Geigy Corporation, Ardsley, N.Y.

[21] Appl. No.: 719,632

[22] Filed: Apr. 4, 1985

Related U.S. Application Data

[63] Continuation of Ser. No. 401,584, Jul. 26, 1982, abandoned.

[30] Foreign Application Priority Data

Jul. 8, 1981 [CH] Switzerland .......................... 5099/81
Jun. 7, 1982 [CH] Switzerland .......................... 3504/82

[51] Int. Cl.[4] .............................................. C07C 79/46
[52] U.S. Cl. ...................... 560/21; 71/108; 564/171; 564/174; 562/434; 558/253; 558/254; 558/255; 558/394
[58] Field of Search ................................ 560/21; 71/108; 260/465 R, 465 D, 465 F, 417 R; 564/171, 174; 562/434

[56] References Cited

U.S. PATENT DOCUMENTS

| | | | |
|---|---|---|---|
| 3,928,416 | 12/1975 | Bayer et al. | 560/21 |
| 4,069,344 | 1/1978 | Karper | 560/21 |
| 4,500,341 | 2/1985 | Forster et al. | 560/21 |

FOREIGN PATENT DOCUMENTS

| | | | |
|---|---|---|---|
| 3295 | 8/1979 | European Pat. Off. | 560/21 |
| 2938595 | 4/1981 | Fed. Rep. of Germany | 560/21 |
| 57-72946 | 5/1982 | Japan | 560/21 |
| 1390295 | 4/1975 | United Kingdom | 560/21 |

*Primary Examiner*—Paul J. Killos
*Attorney, Agent, or Firm*—Edward McC. Roberts; Bruce M. Collins

[57] ABSTRACT

The invention relates to novel phenoxyphenylamino acid derivatives of the formula I

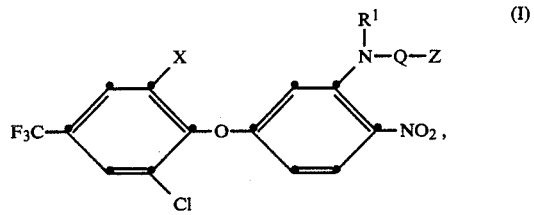

wherein
X is hydrogen, chlorine, fluorine or bromine,
$R^1$ is hydrogen, nitroso, or $C_1$-$C_4$alkyl, $C_2$-$C_4$alkenyl, $C_1$-$C_4$alkylcarbonyl or $C_2$-$C_4$alkenylcarbonyl, each of which is unsubstituted or substituted by one or more halogen atoms,
Q is a straight chain or branched aliphatic radical of 1 to 5 carbon atoms

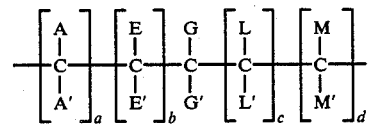

in which A', E', G', L' and M' are hydrogen or $C_1$-$C_4$alkyl, or two adjacent substituents A', E', G', L' and M' together are also a bond between the two carbon atoms to which they are attached; A, E, G, L and M are hydrogen or one or two of A, E, G, L and M are also —$OR^2$, —$SR^3$, —$COOR^4$, $C_1$-$C_4$alkyl or $C_1$-$C_4$alkyl substituted by —$OR^5$, —$SR^6$ or —$COOR^7$, where $R^2$, $R^3$, $R^4$, $R^5$, $R^6$ and $R^7$ are hydrogen or $C_1$-$C_4$alkyl; a, b, c and d are 0 or 1; or $R^1$ and G together are a trimethylene bridge and a, b, c and d are 0; and
Z is —COO⊖Me⊕, —$COOR^8$, —$COSR^8$, —$CONR^9R^{10}$, —$COR^{11}$ or —CN, where Me⊕ is a cation, $R^8$ is hydrogen, $C_1$-$C_8$alkyl which is unsubstituted or substituted by halogen, cyano or $C_1$-$C_4$alkoxy, or is $C_2$-$C_8$alkenyl or $C_3$-$C_8$alkynyl, $R^9$ is hydrogen, $C_1$-$C_4$alkyl or $C_3$-$C_6$cycloalkyl, $R^{10}$ is hydrogen, amino, hydroxyl, $C_1$-$C_4$alkyl which is unsubstituted or substituted by $C_1$-$C_4$alkoxy, or is $C_2$-$C_4$alkynyl, $C_1$-$C_4$alkoxy or $C_3$-$C_6$cycloalkylaminocarbonyl and $R^{11}$ is hydrogen or $C_1$-$C_4$alkyl which is unsubstituted or substituted by $C_1$-$C_4$alkoxy, with the proviso that, in compounds in which simultaneously $R^1$ is hydrogen and a, b, c and d are O, (i) G is —$OR^2$, —$COOR^4$ or $C_1$-$C_4$alkyl which is substituted by —$OR^5$, —$SR^6$ or —$COOR^7$, or (ii) G and G' are both $C_1$-$C_4$alkyl and also to the preparation of these compounds. The compounds of formula I or compositions containing them may be used for controlling undesirable plant growth and for desiccating and defoliating cotton and potato plants.

35 Claims, No Drawings

NOVEL PHENOXYPHENYLAMINO ACID DERIVATIVES, THE PRODUCTION THEREOF, COMPOSITIONS CONTAINING THEM AND USE THEREOF

This application is a continuation of application Ser. No. 401,584, filed July 26, 1982 now abandoned.

The present invention relates to novel phenoxyphenylamino acid derivatives, to the production thereof, to compositions which contain these novel compounds and to the use of said compounds or of compositions containing them for controlling undesirable plant growth or for desiccating or defoliating cotton and potato plants.

Diphenyl ethers having herbicidal properties are known from European patent application No. 27 555, U.S. Pat. No. 4,277,624 and German Offenlegungsschrift No. 2 311 638. Further, phenoxyphenylthioalkanecarboxylic acid derivatives having herbicidal properties are described in European patent application No. 351.

The novel compounds of the present invention have the formula I

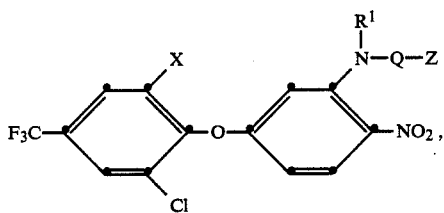

wherein
$X_1$ is hydrogen, chlorine, fluorine or bromine,
$R^1$ is hydrogen, nitroso, or $C_1$–$C_4$alkyl, $C_2$–$C_4$alkenyl, $C_1$–$C_4$alkylcarbonyl or $C_2$–$C_4$alkenylcarbonyl, each of which is unsubstituted or substituted by one or more halogen atoms,
Q is a straight chain or branched aliphatic radical of 1 to 5 carbon atoms

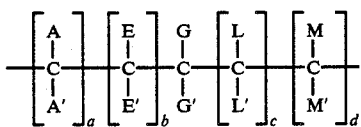

in which A', E', G', L' and M' are hydrogen or $C_1$–$C_4$alkyl, or two adjacent substituents A', E', G', L' and M' together are also a bond between the two carbon atoms to which they are attached; A, E, G, L and M are hydrogen or one or two of A, E, G, L and M are also —$OR^2$, —$SR^3$, —$COOR^4$, $C_1$–$C_4$alkyl or $C_1$–$C_4$alkyl substituted by —$OR^5$, —$SR^6$ or —$COOR^7$, where $R^2$, $R^3$, $R^4$, $R^5$, $R^6$ and $R^7$ arehydrogen or $C_1$–$C_4$alkyl; a, b, c and d are 0 or 1; or $R^1$ and G together are a trimethylene bridge and a, b, c and d are 0; and
Z is —$COO^{\ominus}Me^{\oplus}$, —$COOR^8$, —$COSR^8$, —$CONR^9R^{10}$, —$COR^{11}$ or —CN, where $Me^{\oplus}$ is a cation, $R^8$ is hydrogen, $C_1$–$C_8$alkyl which is unsubstituted or substituted by halogen, cyano or $C_1$–$C_4$alkoxy, or is $C_2$–$C_8$alkenyl or $C_3$–$C_8$alkynyl, $R^9$ is hydrogen, $C_1$–$C_4$alkyl or $C_3$–$C_6$cycloalkyl, $R^{10}$ is hydrogen, amino, hydroxyl, $C_1$–$C_4$alkyl which is unsubstituted or substituted by $C_1$–$C_4$alkoxy, or is $C_2$–$C_4$alkynyl, $C_1$–$C_4$-alkoxy or $C_3$–$C_6$cycloalkylaminocarbonyl and $R^{11}$ is hydrogen or $C_1$–$C_4$alkyl which is unsubstituted or substituted by $C_1$–$C_4$alkoxy, with the proviso that, in compounds in which simultaneously $R^1$ is hydrogen and a, b, c and d are 0, (i) G is —$OR^2$, —$COOR^4$ or $C_1$–$C_4$alkyl which is substituted by —$OR^5$, —$SR^6$ or —$COOR^7$, or (ii) G and G' are both $C_1$–$C_4$alkyl.

$C_1$–$C_4$Alkyl by itself or as moiety of another substituent denotes methyl, ethyl, n-propyl, isopropyl, n-butyl, sec-butyl, tert-butyl and isobutyl; and $C_1$–$C_4$alkoxy is methoxy, ethoxy, n-propoxy, isopropoxy, n-butoxy, sec-butoxy, tert-butoxy and isobutoxy. $C_1$–$C_8$Alkyl comprises the alkyl groups specified above as well as n-pentyl, n-hexyl, n-heptyl, n-octyl and the isomers thereof.

Alkenyl and alkynyl by themselves or as moieties of other substituents comprise the straight chain and branched radicals which come under the indicated number of carbon atoms.

$C_3$–$C_6$Cycloalkyl denotes cyclopropyl, cyclobutyl, cyclopentyl and cyclohexyl.

A suitable cation $Me^{\oplus}$ is preferably the ammonium cation, a metal cation, an organic nitrogen base, a sulfonium cation or a sulfoxonium cation.

Metals suitable for salt formation are alkaline earth metals such as magnesium or calcium, and especially alkali metals such as lithium, potassium and, preferably, sodium. Suitable salt formers are also transition metals, e.g. iron, nickel, cobalt, copper, zinc, chromium or manganese. Examples of organic nitrogen bases which are suitable for salt formation are primary, secondary and tertiary aliphatic and aromatic amines which may be hydroxylated at the hydrocarbon radical, e.g. methylamine, ethylamine, n-propylamine, isopropylamine, the four isomeric butylamines, dimethylamine, diethylamine, di-n-propylamine, diisopropylamine, di-n-butylamine, pyrrolidine, piperidine, morpholine, trimethylamine, triethylamine, tri-n-propylamine, quinuclidine, pyridine, quinoline, isoquinoline, as well as ethanolamine, propanolamine, diethanolamine, or triethanolamine, as well as the quaternary ammonium hydroxides of tetraalkylammonium in which the alkyl moieties independently of one another are straight chain or branched $C_1$–$C_4$alkyl groups, e.g. tetramethylammonium, tetraethylammonium or trimethylethylammonium, and also trimethylbenzylammonium, triethylbenzylammonium and trimethyl-2-hydroxyethylammonium.

By sulfonium and sulfoxonium cations are meant —$^{\oplus}SH_3$ AND —$^{\oplus}S(O)H_3$, in which one or more hydrogen atoms may be replaced by organic radicals, for example the hydrocarbon radicals listed above for the organic nitrogen bases.

Q as a straight chain or branched aliphatic radical of 1 to 5 carbon atoms will be understood as meaning a non-cyclic hydrocarbon radical which is saturated or has olefinic unsaturation, while the indicated number of carbon atoms comprises the substituents A, E, G, L, M, A', E', G', L' and M' only in so far as these are unsubstituted or substituted alkyl radicals.

Where $R_1$ and G together form a trimethylene bridge, a pyrrolidino ring is present.

Preferred compounds of the formula I are those which belong to one of the following groups of compounds:

(a) compounds of formula I, wherein X is hydrogen, chlorine, fluorine or bromine, $R^1$ is hydrogen, nitroso, $C_1$–$C_4$alkyl, or $C_1$–$C_4$alkylcarbonyl which is unsubstituted or substituted by one or more halogen atoms, Q is a straight chain or branched aliphatic radical of 1 to 5 carbon atoms

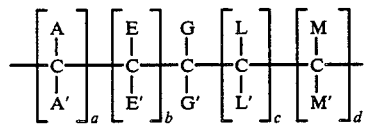

in which A', E', G', L' and M' are hydrogen or $C_1$–$C_4$alkyl, or two adjacent substituents A', E', G', L' and M' together are also a bond between the two carbon atoms to which they are attached; A, E, G, L and M are hydrogen or one or two of A, E, G, L and M are also —$OR^2$, —$SR^3$, —$COOR^4$, $C_1$–$C_4$alkyl or $C_1$–$C_4$alkyl substituted by —$OR^5$, —$SR^6$ or —$COOR^7$, where $R^2$, $R^3$, $R^4$, $R^5$, $R^6$ and $R^7$ are hydrogen or $C_1$–$C_4$alkyl; a, b, c and d are 0 or 1; or $R^1$ and G together are a trimethylene bridge and a, b, c and d are 0; Z is —$COO^\ominus Me^\oplus$, —$COOR^8$, $CONR^9R^{10}$ or —CN, where $Me^\oplus$ is a cation, $R^8$ is hydrogen, $C_1$–$C_4$alkyl which is unsubstituted or substituted by halogen or $C_1$–$C_4$alkoxy, or is $C_2$–$C_4$alkenyl; $R^9$ is hydrogen, $C_1$–$C_4$alkyl or $C_3$–$C_6$cycloalkyl and $R^{10}$ is hydrogen, amino, hydroxyl, $C_1$–$C_4$alkyl which is unsubstituted or substituted by $C_1$–$C_4$alkoxy, or is $C_2$–$C_4$alkynyl, $C_1$–$C_4$alkoxy or $C_3$–$C_6$cycloalkylaminocarbonyl, with the proviso that, in compounds in which simultaneously $R^1$ is hydrogen and a, b, c and d are 0, (i) G is —$COOR^4$ or $C_1$–$C_4$alkyl which is substituted by —$OR^5$, —$SR^6$ or —$COOR^7$, or (ii) G and G' are both $C_1$–$C_4$alkyl;

(b) compounds of formula I, wherein X is hydrogen, chlorine, fluorine or bromine, $R^1$ is hydrogen or $C_1$–$C_4$alkyl, Q is a straight chain or branched alkylene radical of 1 to 5 carbon atoms

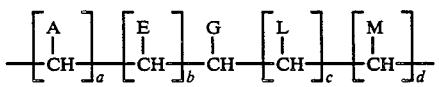

in which A, E, G, L and M are hydrogen or one or two of A, E, G, L and M are also —$OR^2$, —$SR^3$, —$COOR^4$, $C_1$–$C_4$alkyl or $C_1$–$C_4$alkyl substituted by —$OR^5$, —$SR^6$ or —$COOR^7$, where $R^2$, $R^3$, $R^4$, $R^5$, $R^6$ and $R^7$ are hydrogen or $C_1$–$C_4$alkyl; a, b, c and d are 0 or 1; or $R^1$ and G together are a trimethylene bridge and a, b, c and d are 0; and Z is —$COO^\ominus Me^\oplus$, —$COOR^8$, —$CONR^9R^{10}$, —$COR^{11}$ or —CN, where $Me^\oplus$ is a metal cation, $R^8$ is hydrogen or $C_1$–$C_4$alkyl, $R^9$ and $R^{10}$ are hydrogen or $C_1$–$C_4$alkyl and $R^{11}$ is $C_1$–$C_4$alkyl substituted by $C_1$–$C_4$alkoxy, with the proviso that, in compounds in which simultaneously $R^1$ is hydrogen and a, b, c and d are O, G is —$OR^2$, —$COOR^4$ or $C_1$–$C_4$alkyl substituted by —$OR^5$, —$SR^6$ or —$COOR^7$;

(c) compounds of formula I, wherein X is hydrogen, chlorine, fluorine or bromine, $R^1$ is hydrogen or $C_1$–$C_4$alkyl, Q is a straight chain or branched alkylene radical of 1 to 5 carbon atoms.

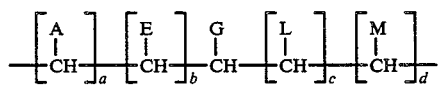

in which A, E, G, L and M are hydrogen or one of A, E, G, L and M is also —$OR^2$, —$SR^3$, —$COOR^4$, $C_1$–$C_4$alkyl or $C_1$–$C_4$alkyl substituted by —$OR^5$, —$SR^6$ or —$COOR^7$, where $R^2$, $R^3$, $R^4$, $R^5$, $R^6$ and $R^7$ are hydrogen or $C_1$–$C_4$alkyl; two of the symbols a, b, c and d are O and the other two are 0 or 1; or $R^1$ and G together are a trimethylene bridge and a, b, c and d are O; and Z is —$COO^\ominus Me^\oplus$, —$COOR^8$, —$COR^{11}$ or —CN, where $Me^\oplus$ is a metal cation, $R^8$ is hydrogen or $C_1$–$C_4$alkyl, and $R^{11}$ is $C_1$–$C_4$alkyl substituted by $C_1$–$C_4$alkoxy, with the proviso that, in compounds in which simultaneously $R^1$ is hydrogen and a, b, c and d are O, G is —$OR^2$, —$COOR^4$ or $C_1$–$C_4$alkyl substituted by —$OR^5$, —$SR^6$ or —$COOR^7$;

(d) compounds of formula I, wherein X is hydrogen or chlorine, $R^1$ is hydrogen, nitroso, methyl, methylcarbonyl, ethylcarbonyl, vinylcarbonyl, chloromethylcarbonyl, trichloromethylcarbonyl or trifluoromethylcarbonyl; Q is a straight chain or branched aliphatic radical of 1 to 5 carbon atoms

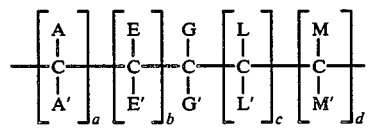

in which A', E', G', L' and M' are hydrogen or $C_1$–$C_4$alkyl, or two adjacent substituents A', E', G', L' and M' together are also a bond between the two carbon atoms to which they are attached; A, E, G, L and M are hydrogen or one of A, E, G, L and M is also —$OR^2$, —$SR^3$, —$COOR^4$, $C_1$–$C_4$alkyl or $C_1$–$C_4$alkyl substituted by —$OR^5$, —$SR^6$ or —$COOR^7$, where $R^2$, $R^3$, $R^4$, $R^5$, $R^6$ and $R^7$ are hydrogen or $C_1$–$C_4$alkyl; a, b, c and d are 0 or 1; or $R^1$ and G together are a trimethylene bridge and a, b, c and d are O; and Z is —$COO^\oplus Me^\ominus$, —$COOR^8$, —$CONR^9R^{10}$ or —CN, where $Me^\oplus$ is a cation, $R^8$ is hydrogen, $C_1$–$C_8$alkyl which is unsubstituted or substituted by halogen or $C_1$–$C_4$alkoxy, or is $C_2$–$C_8$alkenyl or $C_3$–$C_8$alkynyl, $R^9$ is hydrogen, $C_1$–$C_4$alkyl or $C_3$–$C_6$cycloalkyl, $R^{10}$ is hydrogen, amino, hydroxyl, $C_1$–$C_4$alkyl which is unsubstituted or substituted by $C_1$–$C_4$alkoxy, or is $C_2$–$C_4$alkynyl, $C_1$–$C_4$alkoxy or $C_3$–$C_6$cycloalkylaminocarbonyl, with the proviso that, in compounds in which simultaneously $R^1$ is hydrogen and a, b, c and d are O, (i) G is —$COOR^4$ or $C_1$–$C_4$alkyl which is substituted by —$OR^5$, —$SR^6$ or —$COOR^7$, or (ii) G and G' are both $C_1$–$C_4$alkyl;

(e) compounds of formula I, wherein X is hydrogen or chlorine, $R^1$ is hydrogen or methyl, Q is a straight chain or branched alkylene radical of 1 to 5 carbon atoms

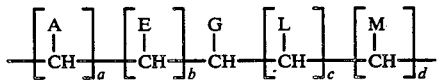

in which A, E, G, L and M are hydrogen or one of the substituents A, E, G, L and M is also —$OR^2$, —$SR^3$, —$COOR^4$, $C_1$–$C_4$alkyl or $C_1$–$C_4$alkyl which is substituted by —$OR^5$, —$SR^6$ or —$COOR^7$, where $R^2$, $R^3$, $R^4$, $R^5$, $R^6$ and $R^7$ are hydrogen or $C_1$–$C_4$alkyl; two of the symbols a, b, c and d are O and the other two are 0 or 1; or $R^1$ and G together are a trimethylene bridge and a, b, c and d are O; and Z is —$COO^\ominus Me^\oplus$, —$COOR^8$, —COR[11] or —CN, where Me⊕ is a metal cation, R[8] is hydrogen or C₁–C₄alkyl and R[11] is C₁–C₄alkyl substituted by C₁–C₄alkoxy, with the proviso that, in compounds in which simultaneously R[1] is hydrogen and a, b, c and d are 0, G is —OR[2], —COOR[4] or C₁–C₄alkyl which is substituted by —OR[5], —SR[6] or —COOR[7];

(f) compounds of formula I, wherein X is hydrogen or chlorine, R[1] is hydrogen, nitroso, or C₁–C₄alkyl, C₂–C₄alkenyl, C₁–C₄alkylcarbonyl or C₂–C₄alkenylcarbonyl, each unsubstituted or substituted by 1 to 3 chlorine or fluorine atoms, or is 1,5-pentamethylene or a straight chain or branched aliphatic radical of 1 to 3 carbon atoms

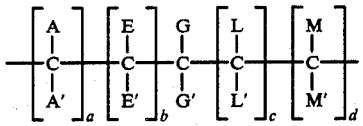

in which A', E', G', L' and M' are hydrogen or one of A', E', G', L' and M' is also C₁–C₄alkyl or two adjacent substituents A', E', G', L' and M' together also are a bond between the two carbon atoms to which they are attached; A, E, G, L and M are hydrogen or one of A, E, G, L and M is also carboxyl, C₁–C₄alkoxycarbonyl, C₁–C₄alkyl which is unsubstituted or monosubstituted by hydroxyl or C₁–C₄alkylthio, two of the symbols a, b, c and d are 0 and the other two are 0 or 1; or R[1] and G together form a trimethylene bridge and a, b, c and d are O; and Z is —COO⊖Me⊕, —COOR[8], —CONR[9]R[10] or —CN, where Me⊕ is an alkali metal cation, R[8] is hydrogen, C₁–C₈alkyl which is unsubstituted or monosubstituted by chlorine or C₁–C₄alkoxy, or is C₂–C₈alkenyl or C₃–C₈alkynyl, R[9] is hydrogen, C₁–C₄alkyl or C₃–C₆cycloalkyl and R[10] is hydrogen, amino, hydroxyl, C₁–C₄alkyl which is unsubstituted or monosubstituted by C₁–C₄alkoxy, or is C₂–C₄alkenyl, C₁–C₄alkoxy or C₃–C₆cycloalkylaminocarbonyl, with the proviso that, in compounds in which simultaneously R[1] is hydrogen and a, b, c, and d are O, (i) G is carboxyl, C₁–C₄alkoxycarbonyl or C₁–C₄alkyl which is monosubstituted by hydroxyl or C₁–C₄alkylthio, or (ii) G and G' are both C₁–C₄alkyl;

(g) compounds of formula I, wherein X is hydrogen, R[1] is hydrogen, Q is a 1,2-ethylene bridge and Z is —COO⊖Me⊕, —COOR[8], COSR[8], —CONR[9]R[10], —COR[11] or —CN, where Me⊕ is a cation, R[8] is hydrogen, C₁–C₈alkyl which is unsubstituted or substituted by halogen, cyano or C₁–C₄alkoxy, or is C₂–C₈alkenyl or C₃–C₈alkynyl, R[9] is hydrogen, C₁–C₄alkyl or C₃–C₆cycloalkyl, R[10] is hydrogen, amino, hydroxyl, C₁–C₄alkyl which is unsubstituted or substituted by C₁–C₄alkoxy, or is C₂–C₄alkynyl, C₁–C₄alkoxy or C₃–C₆cycloalkylaminocarbonyl, and R[11] is hydrogen or C₁–C₄alkyl which is unsubstituted or substituted by C₁–C₄alkoxy;

(h) compounds of formula I, wherein X is hydrogen, chlorine, fluorine or bromine, R[1] is hydrogen, nitroso, or C₁–C₄alkyl, C₂–C₄alkenyl, C₁–C₄alkylcarbonyl or C₂–C₄alkenylcarbonyl, each unsubstituted or substituted by one or more halogen atoms, Q is 1,5-pentamethylene or a straight chain or branched aliphatic radical of 1 to 3 carbon atoms

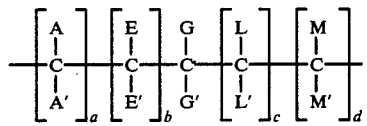

in which A', E', G', L' and M' are hydrogen or one of A', E', G', L' and M' is also methyl, or two adjacent substituents A', E', G', L' and M' together are also a bond between the two carbon atoms to which they are attached; A, E, G, L and M are hydrogen or one of A, E, G, L and M is also carboxyl, methoxycarbonyl, ethoxycarbonyl, methyl, hydroxymethyl, 1-hydroxyethyl, 2-hydroxyethyl or 2-methylthioethyl, two of the symbols a, b, c and d are 0 and the other two are 0 or 1; or R[1] and G together are a trimethylene bridge, and a, b, c and d are 0; and Z is —COO⊖Me⊕, —COOR[8], —CONR[9]R[10] or —CN, where Me⊕ is a sodium cation, R[8] is hydrogen, C₁–C₄alkyl, 2-chloroethyl, 2-methoxyethyl, allyl, or prop-2-ynyl, R[9] is hydrogen, methyl or cyclohexyl, and R[10] is hydrogen, amino, hydroxyl, C₁–C₃alkyl, 2-methylethyl, but-3-yn-2-yl, methoxy or cyclohexylaminocarbonyl, with the proviso that, in compounds in which simultaneously R[1] is hydrogen and a, b, c and d are O, (i) G is carboxyl, methoxycarbonyl, ethoxycarbonyl, hydroxymethyl, 1-hydroxyethyl, 2-hydroxyethyl or methylthioethyl, or (ii) G and G' are both methyl;

(i) compounds of formula I, wherein X is hydrogen or chlorine, R[1] is hydrogen, nitroso, C₁–C₄alkyl, C₁–C₄alkylcarbonyl which is unsubstituted or substituted by 1 to 3 chlorine or fluorine atoms, or is C₂–C₄alkenylcarbonyl; Q is 1,5-pentamethylene or a straight chain or branched aliphatic radical of 1 to 3 carbon atoms

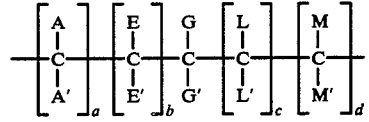

in which A', E', G', L' and M' are hydrogen or one of A', E', G', L' and M' is also C₁–C₄alkyl, or two adjacent substituents A', E', G', L' and M' together are also a bond between the two carbon atoms to which they are attached; A, E, G, L and M are hydrogen or one of A, E, G, L and M is also carboxyl, C₁–C₄alkoxycarbonyl, C₁–C₄alkyl which is unsubstituted or monosubstituted by hydroxyl or C₁–C₄alkylthio, two of the symbols a, b, c and d are 0 and the other two are 0 or 1; or R[1] and G together are a trimethylene bridge and a, b, c, and d are 0; and Z is —COO⊖Me⊕, —COOR[8], —CONR[9]R[10] or —CN, where Me⊕ is an alkali metal cation, R[8] is hydrogen, C₁–C₄alkyl which is unsubstituted or monosubstituted by chlorine or C₁–C₄alkoxy, or is C₂–C₄alkenyl, R[9] is hydrogen, C₁–C₄alkyl or C₃–C₆cycloalkyl and R[10] is hydrogen, amino, hydroxyl, C₁–C₄alkyl, which is unsubstituted or monosubstituted by C₁–C₄alkoxy, or is C₂–C₄alkynyl, C₁–C₄alkoxy or C₃–C₆cycloalkylaminocarbonyl, with the proviso that, in compounds in which simultaneously R[1] is hydrogen and a, b, c and d are 0, (i) G is carboxyl, C₁–C₄alkoxycarbonyl, or C₁–C₄alkyl which is monosubstituted by hydroxyl or C₁–C₄alkylthio, or (ii) G and G' are both C₁–C₄alkyl;

(k) compounds of formula I, wherein X is hydrogen or chlorine, R[1] is hydrogen, nitroso, methyl, methylcarbonyl, ethylcarbonyl, vinylcarbonyl, chloromethylcarbonyl, trichloromethylcarbonyl or trifluoromethylcarbonyl, Q is 1,5-pentamethylene or a straight chain or branched aliphatic radical of 1 to 3 carbon atoms

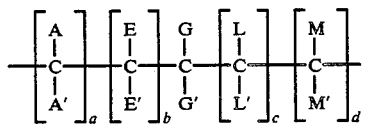

in which A', E', G', L' and M' are hydrogen or one of A', E', G', L' and M' is also methyl, or two adjacent substituents A', E', G', L' and M' together are also a bond between the two carbon atoms to which they are attached; A, E, G, L and M are hydrogen or one of A, E, G, L and M is also carboxyl, methoxycarbonyl, ethoxycarbonyl, methyl, hydroxymethyl, 1-hydroxyethyl, 2-hydroxyethyl or 2-methylthioethyl, two of the symbols, a, b, c and d are 0 and the other two are 0 or 1; or $R^1$ and G together are a trimethylene bridge and a, b, c and d are 0; and Z is —COO⊖Me⊕, —COOR$^8$, —CONR$^9$R$^{10}$ or —CN, where Me⊕ is a sodium cation, R$^8$ is hydrogen, $C_1$-$C_4$alkyl, 2-chloroethyl, 2-methoxyethyl, allyl or prop-2-ynyl, R$^9$ is hydrogen, methyl or cyclohexyl, and R$^{10}$ is hydrogen, amino, hydroxyl, $C_1$-$C_3$alkyl, 2-methoxyethyl, but-3-yn-2-yl, methoxy or cyclohexylaminocarbonyl, with the proviso that, in compounds in which simultaneously $R^1$ is hydrogen and a, b, c and d are 0, (i) G is carboxyl, methoxycarbonyl, ethoxycarbonyl, hydroxymethyl, 1-hydroxyethyl, 2-hydroxyethyl or 2-methylthioethyl, or (ii) G and G' are both methyl;

(1) compounds of formula I, wherein X is hydrogen or chlorine, $R^1$ is hydrogen, nitroso, methyl, methylcarbonyl, ethylcarbonyl, chloromethylcarbonyl, trichloromethylcarbonyl, trifluoromethylcarbonyl, Q is 1,5-pentamethylene or a straight chain or branched aliphatic radical of 1 to 3 carbon atoms

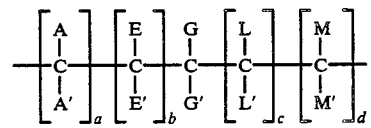

in which A', E', G', L' and M' are hydrogen or one of A', E', G', L' and M' is also methyl, or two adjacent substituents A', E', G', L' and M' together are also a bond between the two carbon atoms to which they are attached; A, E, G, L and M are hydrogen or one of A, E, G, L and M is also carboxyl, ethoxycarbonyl, methyl, hydroxymethyl, 1-hydroxyethyl or 2-methylthioethyl; two of the symbols a, b, c, and d are 0 and the other two are 0 or 1; or $R^1$ and G together are a trimethylene bridge and a, b, c and d are 0; and Z is —COOR$^8$, —CONR$^9$R$^{10}$ or —CN, where R$^8$ is hydrogen, $C_1$-$C_4$alkyl, 2-chloroethyl, 2-methoxyethyl or allyl, R$^9$ is hydrogen, methyl or cyclohexyl, and R$^{10}$ is hydrogen, amino, hydroxyl, $C_1$-$C_3$alkyl, 2-methoxyethyl, but-3-yn-2-yl, methoxy or cyclohexylaminocarbonyl, with the proviso that, in compounds in which simultaneously $R^1$ is hydrogen and a, b, c and d are 0, (i) G is carboxyl, ethoxycarbonyl, hydroxymethyl, 1-hydroxyethyl or 2-methylthioethyl, or (ii) G and G' are both methyl;

(m) compounds of formula I, wherein X is hydrogen, $R^1$ is hydrogen or methyl, Q is an alkylene radical of 1 to 3 carbon atoms

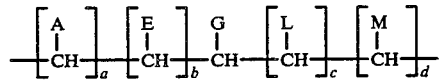

in which A, E, G, L and M are hydrogen or one of A, E, G, L and M is also methyl, hydroxymethyl, 1-hydroxyethyl or 2-methylthioethyl, two of the symbols a, b, c and d are 0 and the other two are 0 or 1; or $R^1$ and G together are a trimethylene bridge and a, b, c and d are 0; and Z is —COOH, —COO—$C_1$-$C_4$alkyl, —COO—$CH_2$—$CH_2$—O—$CH_3$ or —CN, with the proviso that, in compounds in which simultaneously $R^1$ is hydrogen and a, b, c and d are 0, G is hydroxymethyl, 1-hydroxyethyl or 2-methylthioethyl;

(n) compounds of formula I, wherein X is hydrogen, $R^1$ is hydrogen, Q is an ethylene or trimethylene bridge and Z is —COOR$^8$ or —CONR$^9$R$^{10}$, where R$^8$ is hydrogen, $C_1$-$C_3$alkyl or allyl, and R$^9$ and R$^{10}$ are hydrogen.

Particularly preferred compounds are:
methyl N-[2-nitro-5-(2-chloro-4-trifluoromethylphenoxy)phenyl]-3-aminopropionate,
methyl N-[2-nitro-5-(2-chloro-4-trifluoromethylphenoxy)phenyl]-4-amino-n-butyrate,
isopropyl N-[2-nitro-5-(2-chloro-4-trifluoromethylphenoxy)phenyl]-3-aminopropionate,
ethyl N-[2-nitro-5-(2-chloro-4-trifluoromethylphenoxy)phenyl]-3-aminopropionate,
N-[2-nitro-5-(2-chloro-4-trifluoromethylphenoxy)phenyl]-3-aminopropionic acid,
N-[2-nitro-5-(2-chloro-4-trifluoromethylphenoxy)phenyl]-4-amino-n-butyric acid,
3-[N-{2-nitro-5-(2-chloro-4-trifluoromethylphenoxy)phenyl}-amino]-propionamide,
allyl N-[2-nitro-5-(2-chloro-4-trifluoromethylphenoxy)phenyl]-3-aminopropionate.

The compounds of formula I are obtained by
(a) reacting a compound of formula II

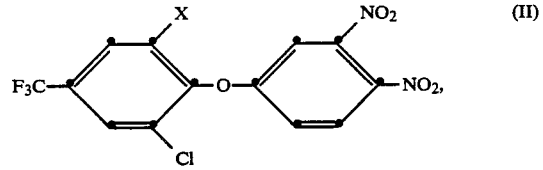

wherein X is as defined for formula I, with a compound of formula III

wherein $R^1$, Q and Z are as defined for formula I, in the presence of a base, or
(b) reacting a compound of formula IV

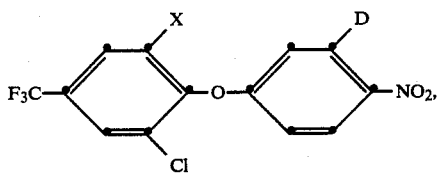

wherein X is as defined for formula I and D is a removable radical, with a compound of formula III

wherein $R^1$, Q and Z are as defined for formula I, or
(c) reacting a compound of formula V

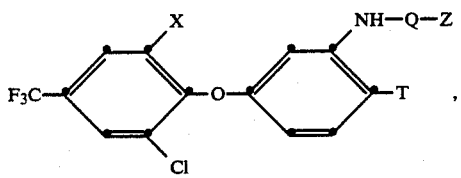

wherein X, Q and Z are as defined for formula I and T is hydrogen or nitro, with an acid hydride or acid chloride and, if T is hydrogen, nitrating the reaction product obtained, to give compounds of formula I, wherein $R^1$ is $C_1$-$C_4$alkylcarbonyl or
(d) reacting a compound of formula VII

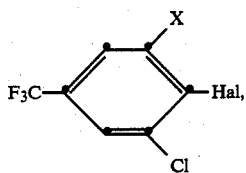

wherein X is as defined for formula I and Hal is a halogen atom, with a compound of the formula VIII

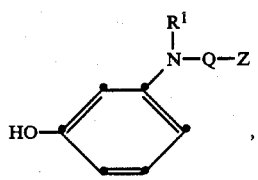

wherein $R^1$, Q and Z are as defined for formula I, in the presence of a base at elevated temperature, and nitrating the reaction product of the formula IX

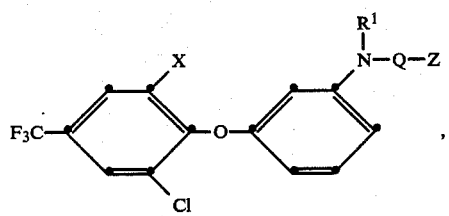

wherein X, $R^1$, Q and Z are as defined for formula I, or
(e) reacting a compound of formula V, wherein X, Q, Z and T are as defined, with a corresponding alkylating agent, to give compounds of formula I, wherein $R^1$ is $C_1$-$C_4$alkyl, and (f) if desired, converting the compounds of formula I, wherein Z is a carboxyl group, in a manner known per se, into the corresponding salts, esters, amides, ketones or nitriles.

The starting compounds of the formulae II, III, IV, V, VI, VII, VIII and IX are known or they may be obtained by methods analogous to known ones.

The reactions according to process variants (a), (b), (c), (d) and (e) may be conducted without or in the presence of solvents or diluents which are inert to the reactants. It is preferred to use organic solvents, e.g. low molecular alcohols, ketones such as methyl ethyl ketone or dimethyl formamide, dimethyl sulfoxide, or chlorinated hydrocarbons, ethers or aromatic hydrocarbons.

The reaction temperatures are in the range from 0° to 200° C., with the preferred range being from 20° to 100° C.

Examples of suitable bases are KOH, $NaOCH_3$, $K_2CO_3$, potassium tert-butylate, or organic bases such as triethylamine.

Examples of suitable removable radicals D in process variant (b) are halogen, a methoxy group, a 2-chloro-4-trifluoromethylphenoxy group or a 2,6-dichloro-4-trifluoromethylphenoxy group.

Suitable alkylating agents are the corresponding alkyl halides or alkyl sulfates.

The nitration of the reaction product of the formula IX is carried out in a manner known per se by treatment with a conventional nitrating acid mixture, e.g. a mixture of concentrated sulfuric acid and nitric acid, or of concentrated sulfuric acid and alkali nitrate salts.

For application as herbicides, desiccants or defoliants, the compounds of formula I are used in unmodified form or, preferably, together with the adjuvants conventionally employed in the art of formulation, and are therefore formulated in known manner to e.g. emulsifiable concentrates, brushable pastes, directly sprayable or dilutable solutions, dilute emulsions, wettable powders, soluble powders, dusts, granulates, and also encapsulations in e.g. polymer substances. Like the nature of the compositions, the methods of application, such as spraying, atomising, dusting, scattering or pouring, are chosen in accordance with the intended objectives and the prevailing circumstances.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalates or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanones, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyl taurin salts.

More frequently, however, so-called synthetic surfactants are used, especially fatty sulfonates, fatty sulfates, sulfonated benzimidazole derivatives of alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine polypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan are also suitable non-ionic surfactants, e.g. polyoxyethylene sorbitan trioleate.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, N.J., 1980, and Sisely and Wood, "Encyclopedia of Surface Active Agents", Chemical Publishing Co., Inc. New York, 1980.

The agrochemical compositions usually contain 0.1 to 99%, preferably 0.1 to 95%, of a compound of the formula I, 1 to 99.9%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients in order to obtain special effects.

The novel compounds of formula I exhibit a herbicidal, in particular a pronounced selective herbicidal, activity against weeds in different crops of cultivated plants, preferably crops of monocots, especially wheat, barley, rye, oats, sorghum, maize and rice. The action of the compounds of formula I in crops of wheat, barley and rice is to be singled out for special mention. The compounds of formula I may be used for controlling weeds pre- and postemergence. The compounds of formula I or compositions containing them are particularly suitable for controlling weeds postemergence in crops of soya beans. A particularly preferred field of use, however, is the selective control of weeds, especially dicot weeds, in crops of cereals, preferably preemergence but also postemergence. Particularly useful compounds for this utility are those in which X and $R^1$ are hydrogen, Q is an ethylene or trimethylene bridge and Z is —COOR$^8$ or —CONR$^9$R$^{10}$, where R$^8$ is hydrogen or $C_1$–$C_3$alkyl and R$^9$ and R$^{10}$ are hydrogen, especially methyl N-[2-nitro-5-(2-chloro-4-trifluoromethylphenoxy)phenyl]-3-aminopropionate, methyl N-[2-nitro-5-(2-chloro-4-trifluoromethylphenoxy)phenyl]-4-amino-n-butyrate, isopropyl N-[2-nitro-5-(2-chloro-4-trifluoromethylphenoxy)phenyl]-3-aminopropionate, ethyl N-[2-nitro-5-(2-chloro-4-trifluoromethylphenoxy)phenyl]-3-aminopropionate, N-[2-nitro-5-(2-chloro-4-trifluoromethylphenoxy)phenyl]-3-aminopropionic acid, N-[2-nitro-5-(2-chloro-4-trifluoromethylphenoxy)phenyl]-4-amino-n-butyric acid, and 3-[N-(2-nitro-5-(2-chloro-4-trifluoromethylphenoxy)phenyl]-aminopropionamide.

The compounds of formula I and compositions containing them are also suitable for desiccating and defoliating cotton and potato plants. Treatment of the plants is made before harvesting, the exact time of treatment depending on various factors, for example age and condition of the plants and climatic conditions. Treatment of the plants is conveniently made about two weeks before harvesting. Particularly suitable for this field of use are compounds of formula I, wherein X and $R^1$ are hydrogen, Q is an ethylene or trimethylene bridge and Z is methoxycarbonyl or allyloxycarbonyl, especially methyl N-[2-nitro-5-(2-chloro-4-trifluoromethylphenoxy)phenyl]-4-amino-n-butyrate, methyl N-[2-nitro-5-(2-chloro-4-trifluoromethylphenoxy)phenyl]-3-aminopropionate and allyl N-[2-nitro-5-(2-chloro-4-trifluoromethylphenoxy)phenyl]-3-aminopropionate.

PREPARATORY EXAMPLES

EXAMPLE 1

N-[2-nitro-5-(2-chloro-4-trifluoromethylphenoxy)phenyl]-4-amino-n-butyric acid (compound 1)

9 g of 3,4-dinitro-2'-chloro-4'-trifluoromethyl-diphenyl ether are stirred in 20 ml of dimethyl sulfoxide, 3 ml of water, 5.1 g of 4-amino-n-butyric acid and 5 ml of 30% sodium hydroxide solution. The mixture is heated briefly to 110° C. to bring the exothermic reaction to completion. The reaction mixture is then poured into about 500 ml of water and extracted once with about 100 ml of toluene. The so purified aqueous phase is acidified with glacial acetic acid and extracted repeatedly with ethyl acetate. The combined ethyl acetate solutions are concentrated to a volume of about 30 ml and the residue is crystallised from about 100 ml of hexane, affording 9 g of N-[2-nitro-5-(2-chloro-4-trifluoromethylphenoxy)phenyl]-4-amino-butyric acid with a melting point of 126°-127° C.

EXAMPLE 2

Methyl N-[2-nitro-5-(2-chloro-4-trifluoromethylphenoxy)phenyl]-4-amino-n-butyrate (compound 2)

8 g of N-[2-nitro-5-(2-chloro-4-trifluoromethylphenoxy)phenyl]-4-amino-n-butyric acid are dissolved in 50 ml of methanol and then 10 ml of concentrated sulfuric acid are slowly added. The reaction mixture is left to stand for some hours, then poured onto ice, made alkaline with sodium hydroxide solution and extracted with toluene. The toluene extract is washed with water until neutral and substantially concentrated in vacuo. The residue is crystallised from hexane, affording 6 g of methyl N-[2-nitro-5-(2-chloro-4-trifluoromethylphenoxy)phenyl]-4-amino-n-butyrate with a melting point of 60°-62° C.

EXAMPLE 3

3-[N-{2-Nitro-5-(2-chloro-4-trifluoromethylphenoxy)phenyl}-amino]propionamide (compound 33)

88 g of N-[2-nitro-5-(2-chloro-4-trifluoromethylphenoxy)phenyl]-3-aminopropionic acid (compound 3) are added to 500 ml of methylene chloride with 34.3 ml of triethylamine at −25° C. With stirring, 22.8 ml of methyl chloroformate are run in over 30 minutes and stirring is continued at −10° to −20° C. After 2 hours, 40 ml of ammonia solution are added and the reaction mixture is warmed to room temperature. The mixture is then washed with water and the organic phase is concentrated. The residue is recrystallised from ethyl acetate/hexane. The product has a melting point of 137°-138° C.

EXAMPLE 4

Methyl N-acetyl-N-[2-nitro-5-(2-chloro-4-trifluoromethylphenoxy)phenyl]-4-amino-n-butyrate (compound 54)

10 g of methyl N-[2-nitro-5-(2-chloro-4-trifluoromethylphenoxy)phenyl]-4-amino-n-butyrate (compound 2) are refluxed in 30 ml of acetyl chloride until the evolution of hydrogen chloride is complete. Excess acetyl chloride is removed in vacuo, affording the title compound in quantitative yield. $n_D^{21} = 1.5437$.

The following compounds of formula I listed in Table 1 together with the compounds of Examples 1 to 4 may also be prepared in analogous manner:

TABLE 1

| Compound | X | $R^1$ | Q | Z | Physical data |
|---|---|---|---|---|---|
| 1 | H | H | —CH₂—CH₂—CH₂— | —COOH | m.p. 126–127° C. |
| 2 | H | H | —CH₂—CH₂—CH₂— | —COOCH₃ | m.p. 60–62° C. |
| 3 | H | H | —CH₂—CH₂— | —COOH | m.p. 105° C. |
| 4 | H | H | —CH(CH₂—OH)— | —COOH | m.p. 179–180° C. |
| 5 | H | H | —CH(CH₃)—CH₂— | —COOH | m.p. 143° C. |
| 6 | H | H | —CH₂—CH(CH₃)— | —COOH | m.p. 118–121° C. |
| 7 | H | H | —CH(CH₂—CH₂—S—CH₃)— | —COOH | m.p. 118° C. |

TABLE 1-continued

Structure: F₃C-phenyl(X, Cl)-O-phenyl(NO₂)-N(R¹)-Q-Z

| Compound | X | R¹ | Q | Z | Physical data |
|---|---|---|---|---|---|
| 8 | H | H | —CH₂—CH₂— | —COOCH₃ | b.p. 240° C./0.15 torr |
| 9 | H | —CH₃ | —CH₂— | —COOH | $n_D^{25}$ 1.5771 |
| 10 | H | —CH₃ | —CH₂— | —COOC₂H₅ | $n_D^{33}$ 1.5751 |
| 11 | H | H | —CH₂—CH₂— | —COOisoC₃H₇ | m.p. 93–95° C. |
| 12 | H | H | —CH₂—CH₂—CH₂— | —COOisoC₃H₇ | b.p. 245° C./0.09 torr |
| 13 | H | H | —CH₂—CH₂— | —COOC₂H₅ | m.p. 93–94° C. |
| 14 | H | H | —CH(CH₃)—CH₂— | —COOsec.C₄H₉ | $n_D^{31}$ 1.5633 |
| 15 | H | H | —CH(HC(CH₃)—OH)— | —COOCH₃ | $n_D^{28}$ 1.5848 |
| 16 | H | H | —CH₂—CH₂— | —COOCH₂—CH₂—O—CH₃ | $n_D^{24}$ 1.5635 |
| 17 | H | H | —CH₂—CH₂—CH₂— | —COOnC₄H₉ | $n_D^{23}$ 1.5695 |
| 18 | H | H | —CH₂—CH₂— | —CN | $n_D^{23}$ 1.5905 |
| 19 | H | | —CH₂—CH₂—CH₂—CH< | —COOH | m.p. 80° C. |
| 20 | H | H | —CH(HC(CH₃)—OH)— | —COOH | m.p. 89–90° C. |
| 21 | H | H | —CH(CH₂—CH₂—OH)— | —COOH | |
| 22 | H | H | —CH(COOCH₃)— | —COOCH₃ | |
| 23 | H | H | —CH₂—CH₂— | —COO⁻Na⁺ | |
| 24 | Cl | H | —CH₂—CH₂— | —COOH | m.p. 151–153° C. |
| 25 | H | H | —CH₂—CH(CH₃)— | —COOC₂H₅ | $n_D^{36}$ 1.5698 |
| 26 | H | —CH₃ | —CH₂— | —COOCH₃ | $n_D^{28}$ 1.5725 |
| 27 | H | H | —CH₂—CH₂—CH₂— | —CONH—CH₃ | m.p. 117–118° C. |
| 28 | H | H | —CH₂—CH₂— | —CONH—C₂H₅ | m.p. 168–170° C. |
| 29 | H | H | —CH₂—CH₂—CH₂— | —CONH—C₃H₇n | m.p. 94–96° C. |
| 30 | Cl | —CH₃ | —CH₂— | —COOH | resin |
| 31 | H | —CH₃ | —CH₂— | —CONH—CH₃ | m.p. 103–105° C. |
| 32 | H | H | —CH₂—CH₂— | —CON(CH₃)₂ | m.p. 101–102° C. |
| 33 | H | H | —CH₂—CH₂— | —CONH₂ | m.p. 137–138° C. |
| 34 | H | H | —CH₂—CH₂—CH₂— | —CONH—C₃H₇iso | m.p. 116–117° C. |
| 35 | H | H | —CH₂—CH₂— | —CN | m.p. 126–127° C. |
| 36 | H | H | —CH(CH₂—CH₂—S—CH₃)— | —COOCH₃ | oil |
| 37 | H | H | —CH(CH₂—CH₂—S—CH₃)— | —CONH₂ | m.p. 118–120° C. |
| 38 | H | —NO | —CH₂—CH₂— | —COOH | m.p. 140° C. |

TABLE 1-continued

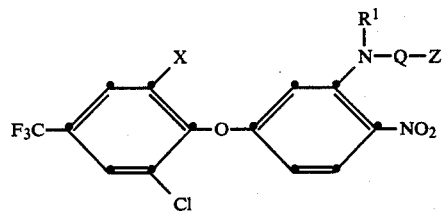

| Compound | X | R¹ | Q | Z | Physical data |
|---|---|---|---|---|---|
| 39 | H | H | —C(CH₃)₂— | —COOH | m.p. 193° C. |
| 40 | H | H | —CH₂—CH₂— | —COOCH₂CH₂Cl | m.p. 73–75° C. |
| 41 | H | —CH₃ | —CH₂— | —COOCH₂CH₂Cl | $n_D^{25.5}$ 1.5701 |
| 42 | H | H | —CH₂—CH₂— | —CONH—NH₂ | m.p. 139–141° C. |
| 43 | H | —NO | —CH₂—CH₂— | —COOCH₃ | $n_D^{25}$ 1.5665 |
| 44 | H | —NO | —CH₂—CH₂— | —CONH—CH₃ | $n_D^{27}$ 1.5525 |
| 45 | H | H | —CH₂—CH₂— | —CON(CH₃)—OCH₃ | m.p. 88–90° C. |
| 46 | H | H | —CH₂—CH₂— | —CON(CH₃)—CH₂CH₂—O—CH₃ | m.p. 104–106° C. |
| 47 | H | H | —CH₂—CH₂— | —CON(CH₃)—CH(CH₃)—C≡CH | resin |
| 48 | H | H | —CH₂—CH₂— | —COOCH₂—CH=CH₂ | m.p. 58–60° C. |
| 49 | H | —CO—CH₂Cl | —CH₂—CH₂— | —COOH | liquid/solid |
| 50 | H | —CO—CH₃ | —CH₂—CH₂— | —COOH | $n_D^{24}$ 1.5465 |
| 51 | H | —CO—CH₂Cl | —CH₂—CH₂—CH₂— | —COOCH₃ | $n_D^{24}$ 1.5483 |
| 52 | H | H | —CH=C(C(O)—OC₂H₅)— | —CN | m.p. 184–185° C. |
| 53 | H | —CO—CF₃ | —CH₂—CH₂—CH₂— | —COOCH₃ | $n_D^{22}$ 1.5215 |
| 54 | H | —CO—CH₃ | —CH₂—CH₂—CH₂— | —COOCH₃ | $n_D^{21}$ 1.5437 |
| 55 | H | H | —CH₂—CH₂—CH₂— | —CONH—OH | m.p. 139–141° C. |
| 56 | H | —CO—CCl₃ | —CH₂—CH₂—CH₂— | —COOCH₃ | resin |
| 57 | H | H | —CH₂—CH₂—CH₂— | —CONH—NH₂ | m.p. 96–99° C. |
| 58 | H | H | —CH₂—CH₂—CH₂— | —CON(cyclohexyl)—CONH(cyclohexyl) | m.p. 148–149° C. |
| 59 | H | —CO—C₂H₅ | —CH₂—CH₂— | —COOCH₃ | oil |
| 60 | H | H | —CH(COOH)—CH₂— | —CONH₂ | m.p. 152–154° C. |
| 61 | H | H | —(CH₂)₅— | —COOH | m.p. 68–72° C. |
| 62 | H | H | —CH₂—CH₂— | —COOCH₂—C≡CH | |
| 63 | H | —CO—CH=CH₂ | —CH₂—CH₂— | —COOC₂H₅ | |

Formulation Examples for liquid active ingredients of the formula I (throughout, percentages are by weight)

5. Emulsifiable concentrates

| | (a) | (b) | (c) |
|---|---|---|---|
| compound of Table 1 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

6. Solutions

| | (a) | (b) | (c) | (d) |
|---|---|---|---|---|
| compound of Table 1 | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| ligroin (boiling range 160–190°) | — | — | 94% | — |

These solutions are suitable for application in the form of microdrops.

| 7. Granulates | (a) | (b) |
|---|---|---|
| compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 8. Dusts | (a) | (b) |
|---|---|---|
| compound of Table 1 | 2% | 5% |
| highly dispersed silicic acid | 1% | 5% |
| talcum | 97% | — |
| kaolin | — | 90% |

Ready for use dusts are obtained by intimately mixing the carriers with the active ingredient.

Formulation examples for solid active ingredients of the formula I (throughout, percentages are by weight)

| 9. Wettable powders | (a) | (b) | (c) |
|---|---|---|---|
| compound of Table 1 | 25% | 50% | 75% |
| sodium lignosulfonate | 5% | 5% | — |
| sodium lauryl sulfate | 3% | — | 5% |
| sodium diisobutylnaphthalene-sulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 10. Emulsifiable concentrate | |
|---|---|
| compound of Table 1 | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50%. |

Emulsions of any required concentration can be obtained from this concentrate by dilution with water.

| 11. Dusts | (a) | (b) |
|---|---|---|
| compound of Table 1 | 5% | 8% |
| talcum | 95% | — |
| kaolin | — | 92% |

Ready for use dusts are obtained by mixing the active ingredient with the carriers, and grinding the mixture in a suitable mill.

| 12. Extruder granulate | |
|---|---|
| compound of Table 1 | 10% |
| sodium lignosulfonate | 2% |
| carboxymethylcellulose | 1% |
| kaolin | 87%. |

The active ingredient is mixed and ground with the adjuvants, and the mixture is subsequently moistened with water. The mixture is extruded and then dried in a stream of air.

| 13. Coated granulate | (a) |
|---|---|
| compound of Table 1 | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 14. Suspension concentrate | |
|---|---|
| compound of Table 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32%. |

The finely ground active ingredient is intimately mixed with the adjuvants, giving a suspension concentrate from which suspensions of any desired concentration can be obtained by dilution with water.

BIOLOGICAL EXAMPLES

EXAMPLE 15

Preemergence herbicidal action (inhibition of germination)

Seeds of test plants are sown in seed dishes in a greenhouse and immediately afterwards the surface of the soil is treated with an aqueous dispersion prepared from a 25% wettable powder formulation of compounds of formula I. Concentrations of 4 kg of active ingredient per hectare are used. The seed dishes are kept in the greenhouse at 22°-25° C. and 50-70% relative humidity, and the test is evaluated after 3 weeks in accordance with the following rating:

1 = plants have not germinated or have completely withered
2-3 = very pronounced action
4-6 = medium action
7-8 = slight action
9 = no action (as untreated controls)

The compounds of formula I are very effective in this test. The action against the weeds Sinapis, Setaria and Stellaria is reported in Table 2.

TABLE 2

| Compound | Sinapis | Setaria | Stellaria |
|---|---|---|---|
| 1 | 1 | 3 | 1 |
| 2 | 1 | 2 | 1 |
| 3 | 1 | 2 | 1 |
| 4 | 3 | 3 | 2 |
| 5 | 1 | 1 | 1 |

TABLE 2-continued

| Compound | Sinapis | Setaria | Stellaria |
|---|---|---|---|
| 6 | 1 | 4 | 1 |
| 8 | 1 | 1 | 1 |
| 9 | 1 | 1 | 2 |
| 10 | 1 | 1 | 2 |
| 11 | 1 | 1 | 1 |
| 12 | 1 | 1 | 1 |
| 13 | 1 | 1 | 1 |
| 14 | 1 | 1 | 1 |
| 15 | 2 | 3 | 5 |
| 16 | 1 | 2 | 1 |
| 17 | 1 | 1 | 1 |
| 18 | 3 | 1 | 1 |
| 24 | 1 | 1 | 1 |
| 25 | 1 | 1 | 1 |
| 26 | 1 | 1 | 1 |
| 27 | 1 | 1 | 1 |
| 28 | 3 | 3 | 1 |
| 29 | 1 | 1 | 1 |
| 31 | 4 | 2 | 2 |
| 32 | 1 | 2 | 1 |
| 33 | 1 | 1 | 1 |
| 34 | 1 | 1 | 1 |
| 38 | 1 | 1 | 1 |
| 39 | 5 | 3 | 1 |
| 40 | 1 | 2 | 1 |
| 41 | 2 | 1 | 2 |
| 42 | 4 | 5 | 1 |
| 43 | 1 | 1 | 1 |
| 44 | 2 | 2 | 2 |
| 45 | 1 | 1 | 1 |
| 46 | 2 | 2 | 2 |
| 48 | 1 | 4 | 1 |
| 49 | 3 | 4 | 3 |
| 50 | 1 | 3 | 2 |
| 54 | 1 | 4 | 1 |

EXAMPLE 16

Preemergence herbicidal action (inhibition of germination)

Under the conditions described in Example 15, a test is carried out with a large number of cultivated plants and weeds using concentrations of 4 kg a.i./ha and 2 kg a.i./ha. The results are evaluated in accordance with the rating employed in Example 15.

The compounds of formula I have a good selective herbicidal action in this test. The results are reported in Tables 3 and 4.

TABLE 3

| Compound 3 | Concentration | |
|---|---|---|
| Test plant | 4 kg/ha | 2 kg/ha |
| barley | 9 | 9 |
| wheat | 9 | 9 |
| maize | 9 | 9 |
| sorghum | 8 | 9 |
| dry rice | 6 | 7 |
| Digitaria sang. | 4 | 7 |
| Echinochloa c.g. | 4 | 4 |
| soya beans | 6 | 8 |
| cotton | 5 | 7 |
| Abutilon | 1 | 1 |
| Sida spinosa | 1 | 2 |
| Amaranthus ret. | 1 | 1 |
| Chenopodium res. | 1 | 1 |
| Solanum nigrum | 1 | 1 |
| Ipomoea | 2 | 3 |
| Sinapis | 1 | 1 |
| Stellaria | 1 | 1 |
| Crysanthem. leuc. | 1 | 1 |
| Galium aparine | 1 | 2 |
| Viola tricolor | 1 | 1 |
| Veronica Sp. | 1 | 1 |

TABLE 4

| Test plant | Compound | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | 1 | | 2 | | 4 | | 8 | | 11 | | 12 | | 13 | | 14 | | 16 | | 19 | | 25 | | 27 | | 33 | | 38 | | 40 | | |
| | kg a.i./ha | | | | | | | | | | | | | | | | | | | | | | | | | | | | | | |
| | 4 | 2 | 4 | 2 | 4 | 2 | 4 | 2 | 4 | 2 | 4 | 2 | 4 | 2 | 4 | 2 | 4 | 2 | 4 | 2 | 4 | 2 | 4 | 2 | 4 | 2 | 4 | 2 | 4 | 2 | |
| wheat | 6 | 9 | 7 | 7 | 9 | 9 | 8 | 9 | 8 | 9 | 9 | 9 | 8 | 9 | 8 | 9 | 7 | 9 | 9 | 9 | 7 | 8 | 6 | 8 | 3 | 4 | 9 | 9 | 9 | 9 | |
| maize | — | — | 8 | 9 | — | — | 9 | 9 | 9 | 9 | 9 | 9 | 8 | 9 | 8 | 9 | 9 | 9 | 9 | 9 | 8 | 9 | 3 | 8 | 3 | 5 | 9 | 9 | 9 | 9 | |
| dry rice | 7 | 8 | 6 | 7 | 6 | 8 | 7 | 7 | 8 | 9 | 9 | 9 | 3 | 6 | 8 | 9 | 7 | 9 | 8 | 9 | 4 | 5 | 7 | 9 | 6 | 7 | 6 | 6 | 7 | 9 | |
| Echinochloa c.g. | 8 | 9 | 3 | 4 | 7 | 8 | 1 | 2 | 2 | 4 | 6 | 9 | 2 | 3 | 2 | 4 | 7 | 9 | 7 | 8 | 1 | 2 | 1 | 2 | 1 | 2 | 6 | 7 | 8 | 9 | |
| soya beans | 6 | 8 | 6 | 7 | 8 | 9 | 7 | 8 | 9 | 9 | 8 | 9 | 9 | 9 | 5 | 7 | 9 | 9 | 9 | 9 | 7 | 8 | 7 | 8 | 6 | 6 | 7 | 9 | 6 | 7 | |
| cotton | — | — | 2 | 8 | — | — | 2 | 2 | 4 | 6 | 3 | 4 | 2 | 3 | 2 | 2 | 9 | 9 | 4 | 6 | 1 | 2 | 2 | 4 | 3 | 4 | 8 | 9 | 4 | 8 | |
| Abutilon | 1 | 1 | 1 | 2 | 1 | 1 | 1 | 1 | 1 | 2 | 1 | 4 | 1 | 1 | 1 | 1 | 1 | 2 | 1 | 3 | 1 | 1 | 1 | 1 | 1 | 1 | 1 | 2 | 1 | 1 | |
| Chenopodium res. | 1 | 1 | 1 | 1 | 1 | 1 | 1 | 1 | 1 | 2 | 1 | 2 | 1 | 1 | 1 | 1 | 1 | 1 | 1 | 1 | 1 | 1 | 1 | 1 | 1 | 1 | 1 | 1 | 1 | 1 | |
| Ipomoea | 4 | 7 | 1 | 2 | 1 | 4 | 1 | 1 | 1 | 2 | 1 | 4 | 1 | 1 | 2 | 2 | 4 | 7 | 3 | 4 | 1 | 2 | 2 | 7 | 2 | 2 | 3 | 3 | 2 | 6 | |
| Sinapis | 1 | 1 | 1 | 1 | 1 | 2 | 1 | 1 | 1 | 1 | 1 | 1 | 1 | 1 | 1 | 1 | 1 | 1 | 1 | 1 | 1 | 1 | 1 | 1 | 1 | 2 | 1 | 1 | 1 | 1 | |
| Galium aparine | 1 | 1 | 1 | 2 | 1 | 3 | 1 | 2 | 2 | 3 | 2 | 3 | 2 | 3 | 2 | 3 | 2 | 4 | 2 | 3 | 2 | 3 | 2 | 3 | 3 | 4 | 1 | 1 | 2 | 3 | |
| Viola tricolor | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | |

EXAMPLE 17

Postemergence herbicidal action (contact herbicide)

The weeds to be tested are sprayed postemergence in the 4- to 6-leaf stage with an aqueous dispersion prepared from compounds of formula I formulated as a 25% wettable powder, at a rate of application of 4 kg a.i./ha. The plants are kept at 24°-26° C. and 45-60% relative humidity. The test is evaluated 15 days later in accordance with the same rating as used in the preemergence test (Example 15).

The compounds of formula I are very effective in this test, as may be seen from the following results:

TABLE 5

| Compound | Setaria | Solanum | Sinapis | Stellaria | Phaseolus |
|---|---|---|---|---|---|
| 1 | 4 | 1 | 1 | 2 | 1 |
| 2 | 2 | 1 | 1 | 1 | 1 |
| 3 | 3 | 1 | 1 | 2 | 1 |
| 4 | 5 | 1 | 3 | 6 | 3 |
| 5 | 4 | 1 | 1 | 1 | 1 |
| 6 | 5 | 1 | 1 | 1 | 2 |
| 7 | 5 | 1 | 1 | 3 | 4 |
| 8 | 1 | 1 | 1 | 1 | 1 |
| 9 | 2 | 1 | 2 | 1 | 2 |
| 10 | 2 | 1 | 1 | 1 | 1 |
| 11 | 6 | 1 | 1 | 1 | 3 |
| 12 | 4 | 1 | 1 | 1 | 2 |
| 13 | 5 | 1 | 1 | 2 | 3 |
| 14 | 2 | 1 | 1 | 2 | 3 |
| 15 | 3 | 1 | 1 | 2 | 2 |
| 16 | 3 | 1 | 1 | 1 | 1 |
| 17 | 3 | 1 | 1 | 1 | 1 | be seen from the following comparison of (a) 0.5 kg a.i./ha according to Table 6 with (b) 0.25 kg a.i./ha and (c) 0.12 kg a.i./ha for a number of compounds:

TABLE 7

| | Compound | | | | | | | | | | | | | | |
|---|---|---|---|---|---|---|---|---|---|---|---|---|---|---|---|
| | 12 | | | 32 | | | 44 | | | 45 | | | 49 | | |
| | Concentration | | | | | | | | | | | | | | |
| Test plants: | a | b | c | a | b | c | a | b | c | a | b | c | a | b | c |
| wheat | 7 | 8 | 9 | 8 | 8 | 9 | 7 | 8 | 8 | 8 | 9 | 9 | 8 | 9 | 9 |
| maize | 6 | 7 | 8 | 6 | 7 | 8 | 6 | 7 | 9 | 7 | 7 | 8 | 5 | 7 | 9 |
| dry rice | 6 | 7 | 8 | 8 | 9 | 9 | 9 | 9 | 9 | 9 | 9 | 9 | 9 | 9 | 9 |
| soya beans | 6 | 6 | 8 | 4 | 7 | 7 | 4 | 7 | 9 | 6 | 6 | 7 | 7 | 7 | 8 |
| Abutilon | 1 | 1 | 2 | 1 | 1 | 1 | 1 | 1 | 1 | 1 | 2 | 2 | 1 | 1 | 1 |
| Xanthium | 1 | 1 | 1 | 1 | 2 | 2 | 1 | 1 | 1 | 1 | 1 | 2 | 1 | 1 | 1 |
| *Chenopodiun res.* | 1 | 1 | 1 | 1 | 1 | 1 | 1 | 2 | 2 | 1 | 2 | 2 | 2 | 2 | 2 |
| Ipomoea | 1 | 1 | 1 | 1 | 1 | 2 | 1 | 1 | 3 | 1 | 1 | 2 | 1 | 1 | 1 |
| Sinapis | 1 | 1 | 1 | 1 | 1 | 1 | 1 | 1 | 1 | 1 | 1 | 2 | 1 | 1 | 1 |
| *Galium aparine* | 1 | 1 | 2 | 2 | 2 | 2 | 2 | 2 | 4 | 1 | 1 | 1 | 1 | 1 | 2 |
| Viola tricolor | 1 | 1 | 1 | 1 | 1 | 1 | 1 | 1 | 1 | 1 | 1 | 1 | 1 | 1 | 1 |

TABLE 5-continued

| Compound | Setaria | Solanum | Sinapis | Stellaria | Phaseolus |
|---|---|---|---|---|---|
| 18 | 4 | 1 | 2 | 2 | 2 |
| 19 | 5 | 1 | 1 | 3 | 4 |
| 24 | 3 | 1 | 1 | 1 | 2 |
| 25 | 1 | 1 | 1 | 1 | 1 |
| 26 | 1 | 1 | 1 | 1 | 1 |
| 27 | 4 | 1 | 1 | 1 | 3 |
| 28 | 4 | 1 | 1 | 1 | 3 |
| 29 | 5 | 1 | 1 | 3 | 4 |
| 30 | 5 | 1 | 1 | 1 | 2 |
| 31 | 3 | 1 | 3 | 2 | 3 |
| 32 | 2 | 1 | 1 | 1 | 3 |
| 33 | 4 | 1 | 1 | 1 | 5 |
| 38 | 4 | 1 | 1 | 1 | 2 |
| 39 | 2 | 1 | 1 | 1 | 1 |
| 40 | 2 | 1 | 1 | 1 | 1 |
| 41 | 2 | 1 | 1 | 1 | 1 |
| 43 | 1 | 1 | 1 | 1 | 1 |
| 44 | 2 | 1 | 1 | 1 | 2 |
| 45 | 1 | 1 | 1 | 1 | 3 |
| 47 | 4 | 1 | 1 | 1 | 3 |
| 48 | 1 | 1 | 1 | 1 | 2 |
| 49 | 2 | 1 | 1 | 1 | 2 |
| 50 | 3 | 1 | 1 | 1 | 2 |
| 51 | 6 | 2 | 1 | 4 | 4 |
| 53 | 4 | 1 | 1 | 3 | 2 |
| 54 | 1 | 1 | 1 | 1 | 1 |

EXAMPLE 18

Postemergence heribicidal action (contact herbicide)

Under the conditions described in Example 17, a test is carried out with a large number of cultivated plants and weeds using a concentration of 0.5 kg a.i./ha. The results are evaluated in accordance with the rating employed in Example 15.

The compounds of formula I are very effective in this test, as may be seen from the following results:

TABLE 6

| | Compound | | | | | | | | | | | | | | |
|---|---|---|---|---|---|---|---|---|---|---|---|---|---|---|---|
| Test plant | 3 | 9 | 11 | 12 | 13 | 27 | 31 | 32 | 33 | 38 | 39 | 44 | 45 | 47 | 49 |
| wheat | 8 | 7 | 9 | 7 | 9 | 9 | 9 | 8 | 9 | 9 | 9 | 7 | 8 | 9 | 8 |
| maize | — | 5 | 9 | 6 | 7 | 9 | 9 | 6 | 8 | 6 | 8 | 6 | 7 | 6 | 5 |
| dry rice | 9 | 8 | 9 | 6 | 8 | 9 | 9 | 8 | 9 | 9 | 9 | 9 | 9 | 9 | 9 |
| soya beans | 6 | 6 | 8 | 6 | 6 | 7 | 8 | 4 | 8 | 6 | 9 | 4 | 6 | 5 | 7 |
| Abutilon | 1 | 1 | 1 | 1 | 1 | 1 | 2 | 1 | 1 | 2 | 7 | 1 | 1 | 2 | 1 |
| Xanthium | 4 | 4 | 1 | 1 | 1 | 6 | 4 | 1 | 4 | 1 | 4 | 1 | 1 | 1 | 1 |
| *Chenopodium res.* | 3 | 2 | 3 | 1 | 2 | 3 | 3 | 1 | 2 | 3 | 2 | 1 | 1 | 1 | 2 |
| Ipomoea | 4 | 3 | 1 | 1 | 1 | 5 | 6 | 1 | 3 | 2 | 2 | 1 | 1 | 2 | 1 |
| Sinapis | 1 | 2 | 2 | 1 | 1 | 4 | 5 | 1 | 3 | 1 | 3 | 1 | 1 | 1 | 1 |
| *Galium aparine* | 4 | 3 | 3 | 1 | 2 | 8 | 4 | 2 | 9 | 2 | 3 | 2 | 1 | 3 | 1 |
| Viola tricolor | 1 | 1 | 1 | 1 | 1 | 1 | 1 | 1 | 2 | 1 | 2 | 1 | 1 | 1 | 1 |

Even at a lower concentration the compounds of formula I have a good selective herbicidal action as may

EXAMPLE 19

Desiccation and defoliation action

Cotton plants of the variety Deltapine are reared in a greenhouse in earthenware pots filled with a mixture of earth and peat. After 12 weeks (start of flowering) the plants are sprayed with aqueous compositions of compounds of formula I at concentrations corresponding to 150, 300 and 600 g a.i./ha (500 l/ha). Untreated plants are used as controls. Evaluation of the test is made 14 days after application of the active ingredients by determining the degree of defoliation (percentage of fallen leaves) and of desiccation (drying out of the leaves remaining on the plant expressed in %), the percentage defoliation always being contained in the percentage desiccation. The compounds of formula I are very effective in this test, especially compounds 2, 8 and 48, as may be seen from Table 8:

TABLE 8

| | | Compound | | |
|---|---|---|---|---|
| | Concentration g/ha | 2 | 8 | 48 |
| defoliation | 150 | 60% | 60% | 80% |
| | 300 | 30% | 70% | 100% |
| | 600 | 70% | 50% | 100% |
| desiccation | 150 | 80% | 80% | 100% |
| | 300 | 90% | 90% | 100% |
| | 600 | 90% | 90% | 100% |

The above compounds are also particularly active in a corresponding test with potato plants.

What is claimed is:

1. A compound selected from the group consisting of an aminoalkanoic acid derivative of the formula:

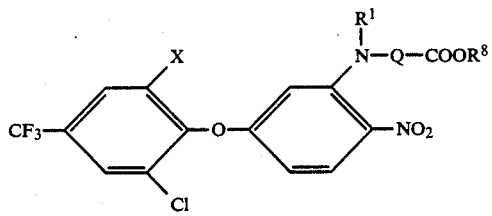

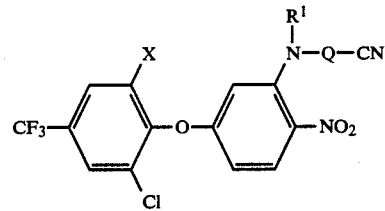

wherein
X is hydrogen, chloro, fluoro or bromo;
R¹ is hydrogen, nitroso, or an unsubstituted or halo substituted alkyl, alkenyl, alkanoyl or alkenoyl group of up to 4 carbon atoms;
Q is straight or branched chained alkylene of 1 to 5 carbon atoms or alkenylene of 2 to 5 carbon atoms which is unsubstituted or substituted with hydroxy, alkylthio of 1 to 4 carbon atoms, carboxy or carbalkoxy in which alkoxy contains 1 to 4 carbon atoms; and
R⁸ is hydrogen, alkyl of 1 to 8 carbon atoms, alkyl of 1 to 8 carbon atoms which is unsubstituted or substituted with halo or alkoxy of 1 to 4 carbon atoms, alkenyl of 2 to 8 carbon atoms, or alkynyl of 3 to 8 carbon atoms; and
the alkali metal, alkaline earth metal, and amine salts thereof when R⁸ is hydrogen.

2. A compound according to claim 1 wherein X is hydrogen or chloro;
R¹ is hydrogen, nitroso, methyl, acetyl, chloroacetyl, trichloroacetyl, trifluoroacetyl or propionyl;
Q is alkylene of 1 to 5 carbon atoms unsubstituted or substituted with carboxy, carbethoxy, hydroxy or methylthio; and
R⁸ is hydrogen, alkyl of 1 to 4 carbon atoms, 2-chloroethyl, 2-methoxyethyl or allyl.

3. A compound according to claim 2 wherein Q is 1,2-ethylene, 1,3-propylene, 1,2-propylene or 2,2-propylidene.

4. A compound according to claim 3 wherein each of X and R¹ is hydrogen and R⁸ is hydrogen, alkyl of 1 to 4 carbon atoms or allyl.

5. Methyl N-[2-nitro-5-(2-chloro-4-trifluoromethylphenoxy)phenyl]-3-aminopropionate according to claim 1.

6. Methyl N-[2-nitro-5-(2-chloro-4-trifluoromethylphenoxy)phenyl]-4-amino-n-butyrate according to claim 1.

7. Isopropyl N-[2-nitro-5-(2-chloro-4-trifluoromethylphenoxy)phenyl]-3-aminopropionate according to claim 1.

8. Ethyl N-[2-nitro-5-(2-chloro-4-trifluoromethylphenoxy)phenyl]-3-aminopropionate according to claim 1.

9. N-[2-Nitro-5-(2-chloro-4-trifluoromethylphenoxy)phenyl]-3-aminopropionic acid according to claim 1.

10. N-[2-Nitro-5-(2-chloro-4-trifluoromethylphenoxy)phenyl]-4-amino-n-butyric acid according to claim 1.

11. 3-[N-{2-Nitro-5-(2-chloro-4-trifluoromethylphenoxy)phenyl}-amino]-propionamide according to claim 1.

12. Allyl N-[2-nitro-5-(2-chloro-4-trifluoromethylphenoxy)phenyl]-3-aminopropionate according to claim 1.

13. A compound of the formula:

wherein
X is hydrogen, chloro, fluoro or bromo;
R¹ is hydrogen, nitroso, or an unsubstituted or halo substituted alkyl, alkenyl, alkanoyl or alkenoyl group of up to 4 carbon atoms; and
Q is straight or branched chained alkylene of 1 to 5 carbon atoms or alkenylene of 2 to 5 carbon atoms which is unsubstituted or substituted with hydroxy, alkylthio of 1 to 4 carbon atoms, carboxy or carbalkoxy in which alkoxy contains 1 to 4 carbon atoms.

14. A compound according to claim 13 wherein
X is hydrogen or chloro;
R¹ is hydrogen, nitroso, methyl, acetyl, chloroacetyl, trichloroacetyl, trifluoroacetyl or propionyl; and
Q is alkylene of 1 to 5 carbon atoms unsubstituted or substituted with carboxy, carbethoxy, hydroxy or methylthio.

15. A compound according to claim 14 wherein Q is 1,2-ethylene, 1,3-propylene, 1,2-propylene or 2,2-propylidene.

16. A compound according to claim 15 wherein each of X and R¹ is hydrogen.

17. A compound of the formula:

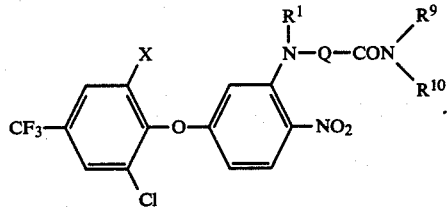

wherein
X is hydrogen, chloro, fluoro or bromo;
R¹ is hydrogen, nitroso, or an unsubstituted or halo substituted alkyl, alkenyl, alkanoyl or alkenoyl group of up to 4 carbon atoms;
Q is straight or branched chained alkylene of 2 to 5 carbon atoms or alkenylene of 2 to 5 carbon atoms which is unsubstituted or substituted with hydroxy, alkylthio of 1 to 4 carbon atoms, carboxy or carbalkoxy in which alkoxy contains 1 to 4 carbon atoms;
R⁹ is hydrogen, alkyl of 1 to 4 carbon atoms or cycloalkyl of 3 to 6 carbon atoms; and
R¹⁰ is hydrogen, amino, hydroxy, alkyl of 1 to 4 carbon atoms which is unsubstituted or substituted with alkoxy of 1 to 4 carbon atoms, alkoxy of 1 to 4 carbon atoms, alkynyl of 2 to 4 carbon atoms, or —CONH-cycloalkyl of 3 to 6 carbon atoms.

18. A compound according to claim 17 wherein
X is hydrogen, or chloro;
R¹ is hydrogen, nitroso, methyl, acetyl, chloroacetyl, trichloroacetyl, trifluoroacetyl or propionoyl;

Q is alkylene of 2 to 5 carbon atoms unsubstituted or substituted with carboxy, carbethoxy, hydroxy, or methylthio;

$R^9$ is hydrogen, methyl or cyclohexyl; and $R^{10}$ is hydrogen, amino, hydroxy, methyl, ethyl, propyl, 2-methoxyethyl or but-3-yn-2-yl.

19. A compound according to claim 18 wherein Q is 1,2-ethylene, 1,3-propylene, 1,2-propylene or 2,2-propylidene.

20. A compound according to claim 19 wherein each of X, $R^9$ and $R^{10}$ is hydrogen.

21. A compound of the formula:

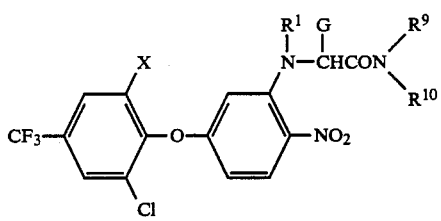

wherein

X is hydrogen, chloro, fluoro or bromo;

$R^1$ is hydrogen, nitroso, or an unsubstituted or halo substituted alkyl, alkenyl, alkanoyl or alkenoyl group of up to 4 carbon atoms;

G is hydroxy, alkoxy of 1 to 4 carbon atoms, carboxy, carbalkoxy wherein alkoxy contains 1 to 4 carbon atoms, or alkyl of 1 to 4 carbon atoms substituted by hydroxy, alkoxy of 1 to 4 carbon atoms, alkylthio of 1 to 4 carbon atoms, carboxy or carbalkoxy wherein alkoxy contains 1 to 4 carbon atoms;

$R^9$ is hydrogen, alkyl of 1 to 4 carbon atoms or cycloalkyl of 3 to 6 carbon atoms; and $R^{10}$ is hydrogen, amino, hydroxy, alkyl of 1 to 4 carbon atoms which is unsubstituted or substituted with alkoxy of 1 to 4 carbon atoms, alkoxy of 1 to 4 carbon atoms, alkynyl of 2 to 4 carbo atoms or —CONH-cycloalkyl of 3 to 6 carbon atoms.

22. A compound according to claim 21 wherein

X is hydrogen or chloro;

$R^1$ is hydrogen, nitroso, methyl, acetyl, chloroacetyl, trichloroacetyl, trifluoroacetyl or propionoyl;

G is hydroxymethyl, 1-hydroxyethyl, 2-hydroxyethyl, 2-methylthioalkyl, or carbethoxy;

$R^9$ is hydrogen, methyl or cyclohexyl; and $R^{10}$ is hydrogen, amino, hydroxy, methyl, ethyl, propyl, 2-methoxyethyl, or but-3-yn-2-yl.

23. A compound according to claim 22 wherein each of X, $R^1$, $R^9$ and $R^{10}$ is hydrogen.

24. A herbicidal composition comprising at least a herbicidally effective amount of a compound according to claim 1 in combination with a carrier therefor.

25. A herbicidal composition comprising at least a herbicidally effective amount of a compound according to claim 17 in combination with a carrier therefor.

26. A method of controlling undesirable plant growth in crops of useful plants which comprises applying to said crops or the the locus thereof a herbicidally effective amount of a compound according to claim 17.

27. A method of desiccating or defoliating cotton or potato plants which comprises applying thereto an effective amount of a compound according to claim 17.

28. A composition according to claim 24, which contains methyl N-[2-nitro-5-(2-chloro-4-trifluoromethylphenoxy)phenyl]-3-aminopropionate as active component.

29. A composition according to claim 24, which contains methyl N-[2-nitro-5-(2-chloro-4-trifluoromethylphenoxy)phenyl]-4-amino-n-butyrate as active component.

30. A composition according to claim 24, which contains isopropyl N-[2-nitro-5-(2-chloro-4-trifluoromethylphenoxy)phenyl]-3-aminopropionate as active component.

31. A composition according to claim 24, which contains ethyl N-[2-nitro-5-(2-chloro-4-trifluoromethylphenoxy)phenyl]-3-aminopropionate as active component.

32. A composition according to claim 24, which contains N-[2-nitro-5-(2-chloro-4-trifluoromethylphenoxy)-phenyl]-3-aminopropionic acid as active component.

33. A composition according to claim 24, which contains N-[2-nitro-5-(2-chloro-4-trifluoromethylphenoxy)-phenyl]-4-amino-n-butyric acid as active component.

34. A composition according to claim 25, which contains 3-[N-{2-nitro-5-(2-chloro-4-trifluoromethylphenoxy)phenyl}amino]-propionamide as active component.

35. A method of desiccating or defoliating cotton or potato plants, which comprises applying thereto an effective amount of a compound of the formula I according to claim 1.

* * * * *